(12) United States Patent
Stohs

(10) Patent No.: US 7,645,742 B2
(45) Date of Patent: Jan. 12, 2010

(54) COMPOSITION FOR ENHANCING CELLULAR ENERGY

(75) Inventor: Sidney Stohs, Carrollton, TX (US)

(73) Assignee: Advocare International, L.P., Carrollton, TX (US)

( * ) Notice: Subject to any disclaimer, the term of this patent is extended or adjusted under 35 U.S.C. 154(b) by 549 days.

(21) Appl. No.: 11/157,991

(22) Filed: Jun. 22, 2005

(65) Prior Publication Data

US 2006/0292134 A1 Dec. 28, 2006

(51) Int. Cl.
*A01N 43/04* (2006.01)
*A61K 31/70* (2006.01)
*A61K 38/43* (2006.01)

(52) U.S. Cl. .................. 514/23; 514/54; 514/440; 514/554; 514/557; 514/565; 514/574; 424/94.1

(58) Field of Classification Search .................. None
See application file for complete search history.

(56) References Cited

U.S. PATENT DOCUMENTS 5,635,535 A * 6/1997 Wagstaff .................. 514/557
2002/0119933 A1 * 8/2002 Butler et al. .................. 514/23

OTHER PUBLICATIONS

Paddon-Jones D. et al., J Nutr. Oct. 2004;134(10 Suppl):2888S-2894S; discussion 2895S, abstract only.
Chromiak, J.A. et al., Nutrition. May 2004;20(5):420-7, abstract only.
Hellsten, Y. et al, Am J Physiol Regul Integr Comp Physiol. Jan. 2004;286(1):R182-8, abstract only.
Falk, D.J. et al, J Strength Cond Res. Nov. 2003;17(4):810-6, abstract only.
Flynn, N.E. et al., Biomed Pharmacother. Nov. 2002;56(9):427-38, abstract only.
Silber, M.L., J Sports Med Phys Fitness. Sep. 1999;39(3):179-88, abstract only.
Zarzeczny, R. et al., J Appl Physiol 91:1775-1781, 2001.
Henderson, G. et al., J Appl Physiol 97: 317-325, 2004.
Lemon, P., Can J Appl Physiol 27(6): 663-680, 2002.
Snell, P. et al., Proceedings of the Fisher Institute for Medical Research, 1(2): 19-23, Feb. 1999.
Huertas, R. et al., Biochemical and Biophysical Research Communications, 188(1): 10-107, 1992.
Siliprandi, N. et al., Biochemia et Biophysica Acta, 1034: 17-21, 1990.
Pauly, D. et al., J Cardiovasc Pharmacol Theraput 5(4): 249-258, 2000.
Omar, M. et al., Creatine Complex as an Athletic Dietary Supplement, Muscle Marketing USA, 2002.
Sugden, M. et al., FASFB Journal, 8: 54-61, 1994.
Brass, E. et al., J Amer Coll Nutr, 17(3): 207-215, 1998.

* cited by examiner

*Primary Examiner*—Traviss C McIntosh, III
(74) *Attorney, Agent, or Firm*—Andreas Baltatzis; Kramer & Amado, PC.

(57) ABSTRACT

A composition for enhancing cellular energy that includes creatine, L-arginine-α-ketoglutarate, D-ribose, L-carnitine, L-citrulline, and pyruvate. The composition is administering to a subject to enhance cellular energy, to increase relative intensity of physical activity performed by the subject, to increase endurance of the subject during the physical activity and to increase the muscle mass of the subject.

10 Claims, 6 Drawing Sheets

FIG.4

| REPS → | 1 | 2 | 3 | 4 | 5 | 6 | 7 | 8 | 9 | 10 |
|---|---|---|---|---|---|---|---|---|---|---|
| REP MAX % → | 100 | 95 | 92.5 | 90 | 87.5 | 85 | 82.5 | 80 | 77.5 | 75 |
| | 97.5 | 92.5 | 90 | 87.5 | 85 | 82.5 | 80 | 77.5 | 75 | 72.5 |
| | 95 | 90 | 87.5 | 85 | 82.5 | 80 | 77.5 | 75 | 72.5 | 70 |
| | 92.5 | 87.5 | 85 | 82.5 | 80 | 77.5 | 75 | 72.5 | 70 | 67.5 |
| | 90 | 85 | 82.5 | 80 | 77.5 | 75 | 72.5 | 70 | 67.5 | 65 |
| | 87.5 | 82.5 | 80 | 77.5 | 75 | 72.5 | 70 | 67.5 | 65 | 62.5 |
| | 85 | 80 | 77.5 | 75 | 72.5 | 70 | 67.5 | 65 | 62.5 | 60 |
| | 82.5 | 77.5 | 75 | 72.5 | 70 | 67.5 | 65 | 62.5 | 60 | 57.5 |
| | 80 | 75 | 72.5 | 70 | 67.5 | 65 | 62.5 | 60 | 57.5 | 55 |
| | 77.5 | 72.5 | 70 | 67.5 | 65 | 62.5 | 60 | 57.5 | 55 | 52.5 |
| | 75 | 70 | 67.5 | 65 | 62.5 | 60 | 57.5 | 55 | 52.5 | 50 |
| | 72.5 | 67.5 | 65 | 62.5 | 60 | 57.5 | 55 | 52.5 | 50 | 47.5 |
| | 70 | 65 | 62.5 | 60 | 57.5 | 55 | 52.5 | 50 | 47.5 | 45 |
| | 67.5 | 62.5 | 60 | 57.5 | 55 | 52.5 | 50 | 47.5 | 45 | 42.5 |
| | 65 | 60 | 57.5 | 55 | 52.5 | 50 | 47.5 | 45 | 42.5 | 40 |
| | 62.5 | 57.5 | 55 | 52.5 | 50 | 47.5 | 45 | 42.5 | 40 | 37.5 |
| | 60 | 55 | 52.5 | 50 | 47.5 | 45 | 42.5 | 40 | 37.5 | 35 |
| | 57.5 | 52.5 | 50 | 47.5 | 45 | 42.5 | 40 | 37.5 | 35 | 32.5 |
| | 55 | 50 | 47.5 | 45 | 42.5 | 40 | 37.5 | 35 | 32.5 | 30 |
| | 52.5 | 47.5 | 45 | 42.5 | 40 | 37.5 | 35 | 32.5 | 30 | 27.5 |
| | 50 | 45 | 42.5 | 40 | 37.5 | 35 | 32.5 | 30 | 27.5 | 25 |
| | 47.5 | 42.5 | 40 | 37.5 | 35 | 32.5 | 30 | 27.5 | 25 | 22.5 |
| | 45 | 40 | 37.5 | 35 | 32.5 | 30 | 27.5 | 25 | 22.5 | 20 |
| | 42.5 | 37.5 | 35 | 32.5 | 30 | 27.5 | 25 | 22.5 | 20 | 17.5 |
| | 40 | 35 | 32.5 | 30 | 27.5 | 25 | 22.5 | 20 | 17.5 | 15 |
| | 37.5 | 32.5 | 30 | 27.5 | 25 | 22.5 | 20 | 17.5 | 15 | 12.5 |
| | 35 | 30 | 27.5 | 25 | 22.5 | 20 | 17.5 | 15 | 12.5 | 10 |
| | 32.5 | 27.5 | 25 | 22.5 | 20 | 17.5 | 15 | 12.5 | 10 | 7.5 |
| | 30 | 25 | 22.5 | 20 | 17.5 | 15 | 12.5 | 10 | 7.5 | 5 |
| | 27.5 | 22.5 | 20 | 17.5 | 15 | 12.5 | 10 | 7.5 | 5 | 2.5 |
| | 25 | 20 | 17.5 | 15 | 12.5 | 10 | 7.5 | 5 | 2.5 | 0 |
| | 22.5 | 17.5 | 15 | 12.5 | 10 | 7.5 | 5 | 2.5 | 0 | |
| | 20 | 15 | 12.5 | 10 | 7.5 | 5 | 2.5 | 0 | | |
| | 17.5 | 12.5 | 10 | 7.5 | 5 | 2.5 | 0 | | | |
| | 15 | 10 | 7.5 | 5 | 2.5 | 0 | | | | |
| | 12.5 | 7.5 | 5 | 2.5 | 0 | | | | | |
| | 10 | 5 | 2.5 | 0 | | | | | | |
| | 7.5 | 2.5 | 0 | | | | | | | |
| | 5 | 0 | | | | | | | | |
| | 2.5 | | | | | | | | | |
| | 0 | | | | | | | | | |

Relative Intensity

COMPOSITION FOR ENHANCING CELLULAR ENERGY

BACKGROUND OF THE INVENTION

1. Field of the Invention

The present invention generally relates to a composition for enhancing cellular energy. More particularly, the invention relates to a composition for enhancing cellular energy that can be administered to a subject in order to enhance performance and endurance during physical activity.

2. Description of Related Art

Nutritional supplementation plays an ever increasing role in the advancement of exercise, health and fitness. Performance elite, fitness minded and/or well-oriented individuals seeking healthier lifestyles use nutritional supplements as safe and legal avenues to boost their performance and endurance while performing physical activities. Properly formulated compositions not only may enhance physical performance but also maximize efficiency of physical effort in order to achieve users' health goals such as decreased body fat or weight, increased strength and muscle size, improved body appearance, increased speed and/or generally improved health. However, compositions that are not properly formulated and lack the proper amounts of ingredients, or include improper ingredients, are at best ineffective in assisting users in achieving their goals. At worst, nutritional supplements that lack the correct formulation of ingredients can lead to serious side effects.

One target for producing nutritional supplements that enhance physical performance and endurance has been the cellular energy production mechanisms of the body, particularly those located in muscle cells. The energy production sequences involve an intricate pathway of priming the mechanisms prior to physical activity, providing energy and nutrients during physical activity; and re-energizing, recovering, repairing, and developing the energy producing mechanisms of the body once the physical activity is complete. A number of compositions in the prior art have been proposed to enhance particular aspects of the cellular energy pathway, however there are no compositions that seek to enhance and supplement the cellular energy pathway from beginning to end. In particular there are no compositions that contain the proper amount of the nutrients and energy precursors needed to prepare the body for physical activity; that provide energy and nutrients to the body during physical activity; and that provide the body the materials needed to re-energize, rebuild and improve after the physical activity is complete.

Accordingly, there is a need for a composition that supports metabolic processes; enhances physical performance and endurance; helps maintain and restore energy supplies during and after physical activity; supplies essential components for muscle gain during and after physical activity; and helps manage oxidative stress. Furthermore, there is a need that the composition is easily administered and the components of the composition are in a form that quickly becomes bioavailable to the user. There is also a need for a composition that enhances physical performance and lacks any adverse side effects.

SUMMARY OF THE INVENTION

In light of the present need for composition for enhancing cellular energy, a brief summary of the present invention is presented. Some simplifications and omission may be made in the following summary, which is intended to highlight and introduce some aspects of the present invention, but not to limit its scope. Detailed descriptions of a preferred exemplary embodiment adequate to allow those of ordinary skill in the art to make and use the invention concepts will follow in later sections.

The present invention relates to a composition for enhancing cellular energy comprising creatine, L-arginine-α-ketoglutarate, D-ribose, L-carnitine, L-citrulline and pyruvate. The composition may also include one or more of the following compounds: α-lipoic acid, L-aspartate, succinate, glucomannan, and coenzyme Q10. In order to increase ease of administration and bioavailability of the ingredients, the composition may include an effervescent. Furthermore, the present invention relates to a method for enhancing performance and endurance of a subject during physical activity and increasing the subject's relative intensity of physical activity by administering the composition for enhancing cellular energy.

BRIEF DESCRIPTION OF THE DRAWINGS

Additional advantages and features of the present invention will become apparent from the subsequent description and the appended claims, taken in conjunction with the accompanying drawings, wherein:

FIG. 4 illustrates a relative intensity scale.

DETAILED DESCRIPTION OF THE PREFERRED EMBODIMENTS OF THE INVENTION

The present invention relates to a composition for enhancing cellular energy. The composition incorporates a number compounds that, when combined together, provide a synergistic effect enhancing the cellular energy pathway from beginning to end.

In an embodiment of the invention, the composition includes a combination of the following compounds: creatine, L-arginine-α-ketoglutarate, D-ribose, L-carnitine, L-citrulline and pyruvate. Each of the compounds plays an important role in the composition as they are combined to provide a synergistic effect that does not occur when individual elements are missing.

The target of the invention is the cellular energy pathway, which converts energy containing compounds such as carbohydrates (in the form of glucose) and fats (in the form of fatty acids) into energy that is usable by the body. The breakdown of both of these groups of compounds results in the production of adenosine triphosphate ("ATP"). ATP production is critical for enhancing performance and endurance of physical activity as ATP provides the single source of energy used by the muscles. ATP activity may be characterized by four phases. The first phase is a rapid dephosphorylation of ATP into adenosine diphosphate ("ADP") by the muscle cells. The next step is the regeneration of ATP in the muscle by creatine kinase that rephosphorylates ADP to ATP by transferring a phosphate group from creatine phosphate. The third phase is the anaerobic production of ATP through the production of lactate. The fourth phase is the aerobic restoration of ATP through degradation of Acetyl-CoA in the Krebs cycle (citric acid cycle) and the oxidative phosphorylation of ADP to ATP.

Figure 1:
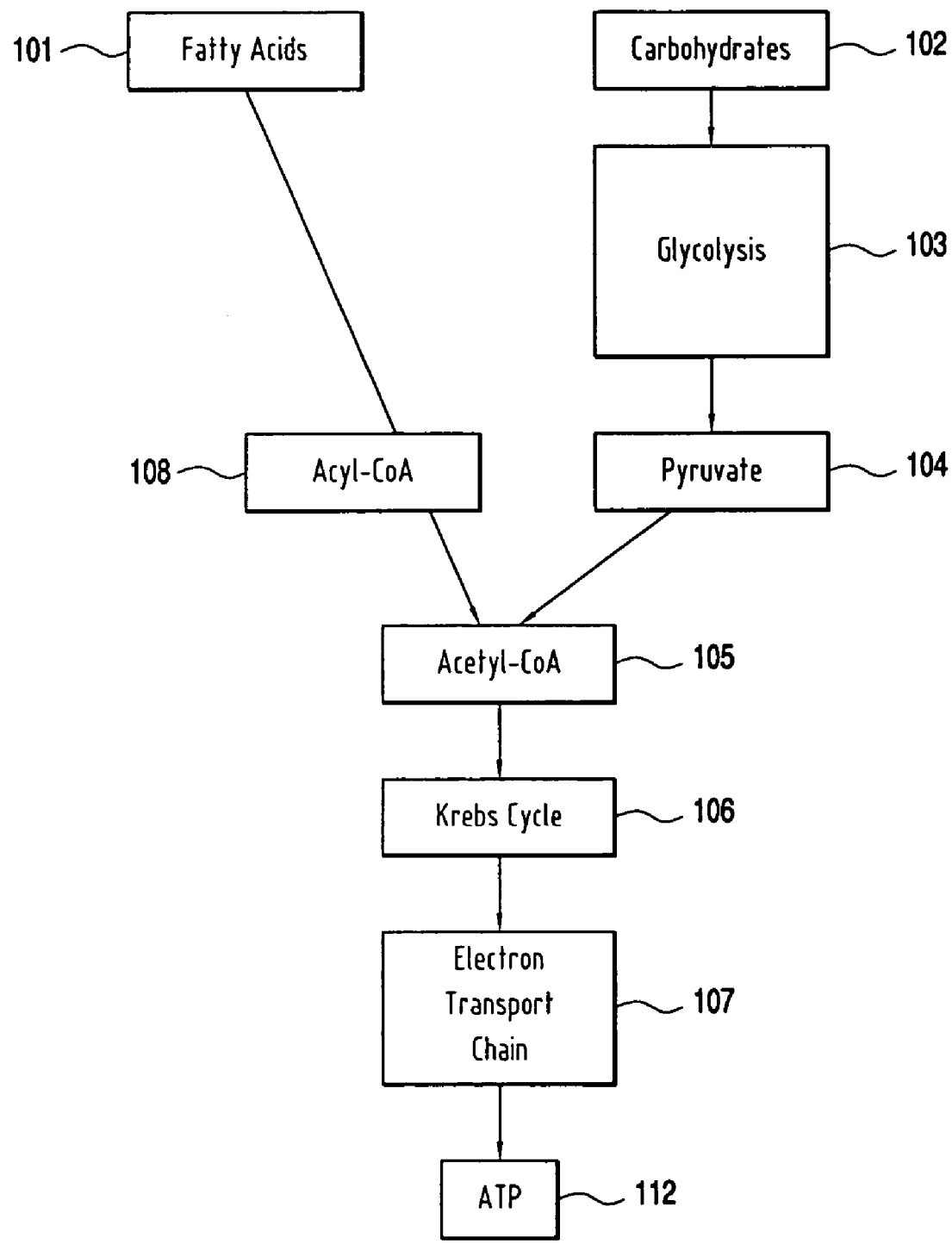
FIG. 1 illustrates a flow chart of the primary cellular energy production mechanisms.

FIG. 1 illustrates a flow chart of the primary cellular energy production mechanisms. In particular, FIG. 1 illustrates the breakdown of fatty acids 101 and carbohydrates 102 by cellular energy mechanisms. Carbohydrates 102 are metabolized through glycolysis 103 into pyruvate 104 and then acetyl-CoA 105, progressing through the Krebs cycle 106 into oxidative phosphorylation through the electron transport chain 107. The final result of this project is the production of ATP 112. Fatty acids 101 do not undergo glycolysis, as seen in FIG. 1, and instead are converted to acyl-CoA 108 and then acetyl-CoA 105 before entering the Krebs Cycle 106. The breakdown of both compounds also produces the reducing compounds $NADH^+$ and $FADH_2^+$ which drive the electron transport chain leading to most efficient production of ATP. The components of the invention all play important roles in the cellular energy pathway as described above. However, proper supplementation results in the increased efficiency and productivity of these energy pathways.

D-Ribose is one of the building blocks of the nucleotides, such as deoxyribose and adenine and adenosine nucleotides such as ATP and ADP. D-ribose compounds are classified as monosaccharides, aldoses, pentoses and reducing sugars. As a building block of nucleotides, D-ribose is used by cells to resynthesize adenine nucleotides and salvage and preserve nucleotide pools. The body's ability to resynthesize ATP may be dependent on the supply of D-ribose in the muscles which is critical for the building the structure of nucleotides.

Figure 2:
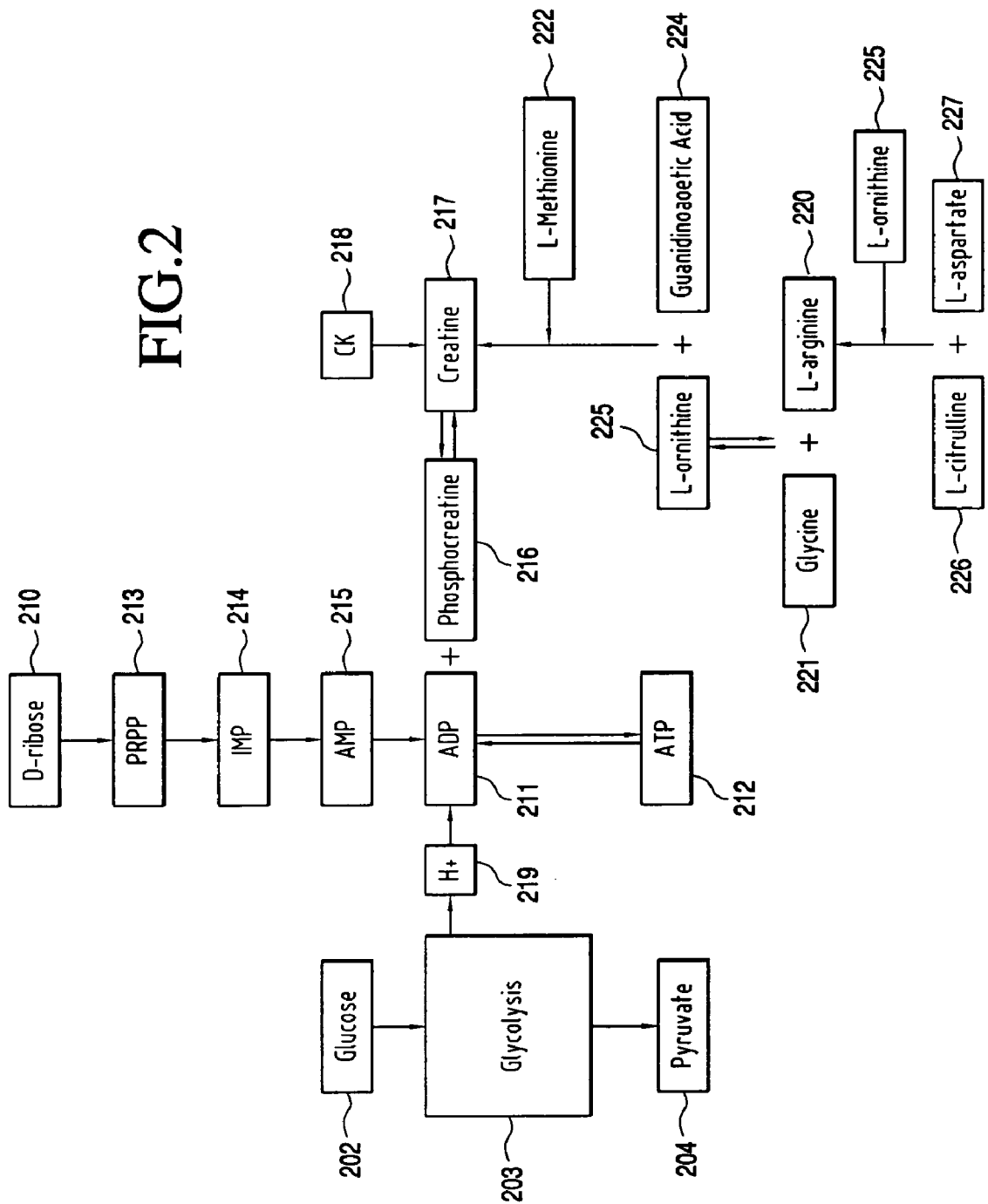
FIG. 2 illustrates a flow chart of the production of ATP.

FIG. 2 illustrates a flow chart of the production of ATP by utilizing D-ribose, creatine and L-arginine. In particular, FIG. 2 illustrates the pathway by which D-ribose 210 is used to produce ATP 212 through the production of ADP 215. In supraphysiological amounts, D-ribose 210 serves as a precursor to phosphoribosyl 1-pyrophosphate ("PRPP") 213. PRPP 213 is a key intermediate in the de novo and salvage pathways of purine nucleotide formation, as well as a key intermediate in synthesis of pyrimidine nucleotides. PRPP 213 is a biochemically activated form of D-ribose 210 and is synthesized from D-ribose-5-phosphate, which is produced in the oxidative pentose phosphate pathway ("PPP"). The limiting step in the PPP is the glucose-6-phosphate dehydrogenase ("G-6-PD") reaction. The G-6-PD reaction can be bypassed with D-ribose 210. Activated PRPP 213 leads to the increased formation of ATP 212 by being converted to inosine monophosphate ("IMP") 214 which is then converted to ADP 215, which is reversibly phosphorylated by phosphocreatine (creatine phosphate) 216 to form ATP 212.

Where D-ribose is not used as a precursor for nucleotide synthesis, D-ribose may be rapidly metabolized and converted into body glucose via the pentose phosphate pathway. By following the conversion process, D-ribose causes a lowering of blood glucose, presumably by inhibiting the enzyme phosphoglucomutase. As compared to other pentoses, D-ribose provides a lower insulin response. The characteristics of D-ribose lead to the properties of increasing concentrations of ADP and ATP, restoring energy and supporting cardiovascular health.

FIG. 2 also illustrates the important role of creatine 217 in cellular energy production. Creatine 217 is composed of the amino acids L-arginine 220, glycine 221 and L-methionine 222 and used in ATP build-up and turnover. This natural substance is primarily found in fish and meat. The body produces creatine 217 whereby L-arginine 220 and glycine 221 form L-ornithine 225. The body combines L-ornithine 225 with guanidinoacetic acid 224 and modified L-methionine 222 to form creatine 217. In muscle and nerve, most of the creatine 217 is phosphorylated to phosphocreatine 216 in a reaction that is catalyzed by the enzyme creatine kinase ("CK") 218. There are three isoforms (isoenzymes) of CK. CK-MM is the skeletal muscle isoform; CK-BB, the brain isoform, and CK-MB, the isoform found in cardiac muscle. Most of the phosphocreatine in the body is in skeletal muscle. The body uses phosphocreatine as a reservoir of chemical energy for the rapid phosphorylation of ADP to reconstitute ATP during vigorous muscle contraction.

Creatine 217, creatine kinase 218 and phosphocreatine 216 make up an intricate cellular energy buffering and transport system connecting sites of energy production in the mitochondria with sites of energy consumption. Creatine kinase 218 is a key enzyme involved in cellular energy homeostasis. As illustrated in FIG. 2, creatine kinase 218 reversibly catalyzes the transfer of the high-energy phosphate bond in phosphocreatine 216 to ADP 211, thereby producing ATP 212. Creatine kinase 218 also catalyzes the reverse reaction, i.e. the transfer of the high-energy phosphate bond in ATP 212 to creatine 217 to form phosphocreatine 216. The reversible reaction may be shown as:

$$Phosphocreatine + ADP + H^+ \leftrightarrows ATP + creatine$$

The energy for the reaction for forming ATP 212 is provided by the body in the form of $H^+$ 219 generated during specific phases of the cellular energy pathway such as glycolysis forming $H^+$ 219 and the electron transport chain. Creatine may also be used to phosphorylate ADP into ATP with energy produced by the electron transport chain which follows the Krebs Cycle in the same reversible reaction cited above.

During periods of intense exercise and skeletal muscle contraction, bioenergetic metabolism switches from one in which oxidative phosphorylation is the major pathway of ATP production to one in which anaerobic glycolysis becomes dominant. Much less ATP would be generated during this period if it were not for phosphocreatine being the only fuel available to regenerate ATP during this period. Thus the availability of phosphocreatine is the limiting factor of skeletal-muscle performance during high intensity and brief bursts (about 10 seconds) of activity. Supplemental creatine may increase phosphocreatine levels in skeletal muscle and enhance ATP turnover during maximal exercise.

L-Arginine-α-ketoglutarate is a complex of the amino acid L-arginine and the sugar α-ketoglutarate. L-arginine is a conditionally essential amino acid that plays a number of important roles in body functions including protein synthesis and detoxification of ammonia formed during the nitrogen catabolism of amino acids via the formation of urea.

FIG. 2 illustrates the synthesis of L-arginine 220 from L-ornithine 225, L-citrulline 226 and L-aspartate 227. Additionally, L-arginine is required for the formation of creatine and other critical compounds for body function, such as nitric oxide, polyamines, L-glutamate, L-proline, agmatin (a possible neurotransmitter in the brain) and the L-arginine-containing tetrapeptide tuftsin. FIG. 2 illustrates the production of creatine 217 from L-arginine 220 as discussed above. When excess L-arginine exists in the body, the glycogenic amino acid can be converted to D-glucose and glycogen or it can be catabolized to produce biological energy.

L-arginine enhances exercise through two different mechanisms. One mechanism is the increase of muscle protein synthesis through increased muscle blood flow caused by the stimulation of nitric oxide. However, it has been found that L-arginine supplementation alone is not an effective supplement to stimulate muscle protein and must be combined with other amino acids. The other mechanism of muscle protein synthesis is as a precursor of a number of important amino acids, including creatine as illustrated in FIG. 2.

Alpha-ketoglutarate is formed form L-glutamine and L-ornithine. The acid form, or α-ketoglutaric acid, is an important intermediate in the Krebs Cycle. The compound has been shown as a vehicle for delivering exogenous low molecular biologically-active compounds, including creatine and L-ornithine that enhances the utilization of these amino acids in the body. Alpha-ketoglutarate in particular has been complexed with L-ornithine and used as a supplement for increasing L-arginine production. Additionally, α-ketoglutarate inhibits arginase which breaks down L-arginine, therefore leading to higher L-arginine concentrations and increased nitric oxide production.

L-citrulline is an amino acid found primarily in the liver. FIG. 2 illustrates the function of L-citrulline 226 as a key precursor in the formation of L-arginine 220 in the body and an early precursor in creatine 217 formation. The amino acid plays a major role in the urea cycle where it detoxifies ammonia. L-citrulline has also been found to function as a precursor of growth hormones and an enhancer of nitric oxide synthesis through its role in boosting L-arginine production.

L-carnitine is a derivative of the essential amino acids L-lysine and L-methionine and is primarily synthesized in the liver and also in the kidneys, and must be transported to other tissues. Niacin, vitamins B6 and C, and iron are involved in L-carnitine's biosynthesis. L-carnitine is described as a conditionally essential nutrient. While humans naturally synthesize L-carnitine, the demands of increased physical activity often exceed an individual's capacity to synthesize the nutrient, therefore supplementation may be necessary to achieve higher levels of exercise.

Figure 3:
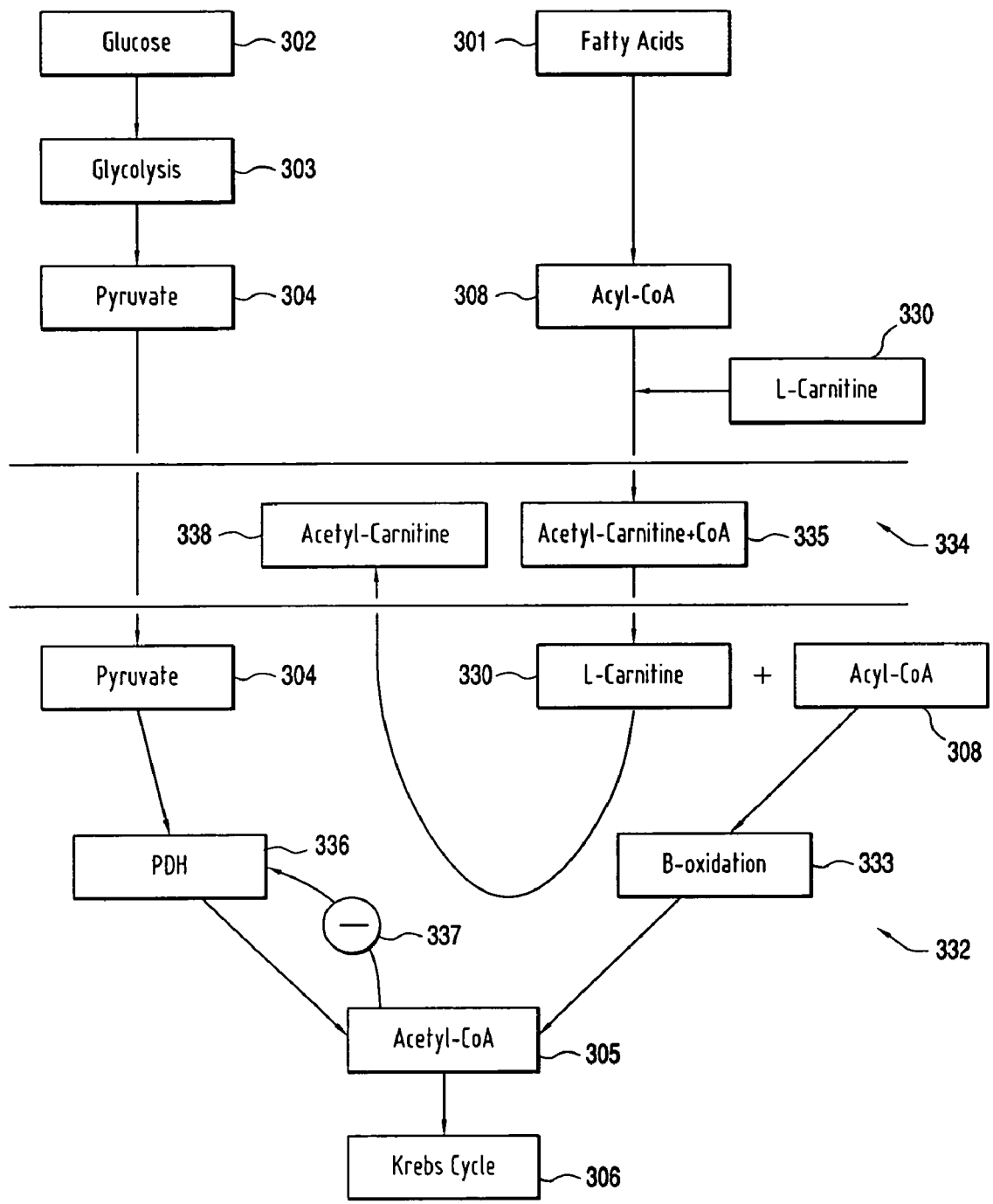
FIG. 3 illustrates a flow chart of the production of Acetyl-CoA.

FIG. 3 illustrates a flow chart of the production of acetyl-CoA. In particular, FIG. 3 illustrates the critical role that L-carnitine 330 plays in cellular energy production by assisting in the formation of acetyl-CoA 305, the key fuel for the aerobic energy production through the Krebs cycle 306. L-carnitine 330 is instrumental in forming acetyl-CoA 305 by two different methods. First chaperoning activated fatty acids (acyl-CoA) 308 into the mitochondrial matrix 332 for metabolism, where the acyl-CoA 308 metabolized into acetyl-CoA 305 through β-oxidation 333. L-carnitine 330 performs the chaperoning function through the carnitine acyltransferase-mediated reversible transfer of carboxylic acids, or acyl groups, between carnitine and coenzyme A in reactions of the following form:

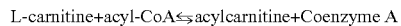

L-carnitine+acyl-CoA⇌acylcarnitine+Coenzyme A

Acyl-carnitine 335 may then pass through the mitochondrial membrane 334 into the mitochondrial matrix 332. The activated fatty acids in the form of acyl-CoA 208 are then processed by beta-oxidation 333 to convert into acetyl-CoA 305 which is the primary fuel for the Krebs Cycle 306.

Following the delivery of long-chain fatty acids into the mitochondria, L-carnitine, either by itself or esterified to an acyl group, recrosses the mitochondrial membrane to allow for continual use in a shuttle process. Another function of L-carnitine is to remove short-chain and medium-chain fatty acids from the mitochondria in order to maintain coenzyme A levels in these organelles. These fatty acids accumulate as a result of normal and abnormal metabolism. This mechanism prevents the build-up in the mitochondria of short-chain and medium-chain fatty acids that may interfere with the bioenergy-producing process vital to the normal function of the cell.

In another method for forming acetyl-CoA 305, carnitine 330 enables the catalytic conversion of pyruvate 304 into acetyl-CoA 305 through the action of pyruvate dehydrogenase ("PDH") 336. Pyruvate dehydrogenase activity is essential to driving aerobic energy production as opposed to the less efficient anaerobic energy production. Overabundant acetyl-CoA 305 provides a negative feedback mechanism 337 that inhibits the activity of PDH 336. L-carnitine 330 removes excess acetyl-CoA 305 in the form of acetylcarnitine 338 from the mitochondrial matrix 332 and thereby preventing the inhibition of PDH 336. By preventing the inhibition of PDH 336, L-carnitine 330 further increases the efficiency of the cellular energy pathways. Increased PDH activity also leads to increased activity of respiratory chain enzymes such as NADH cytochrome-c reductase, succinate cytochrome-c reductase and cytochrome-c oxidase in muscle cells.

L-carnitine supplementation has been shown to increase efficient utilization of pyruvate and acyl-CoA by maximizing aerobic energy production and reducing aerobic energy production as evidenced by decreased levels of plasma lactate and pyruvate.

During exercise of long duration, the increased esterification of muscle L-carnitine reduces the free L-carnitine pool in muscle leading to L-carnitine insufficiency. L-carnitine supplementation therefore prevents depletion of the free L-carnitine pool and allows continued cellular energy production through the mitochondrial system.

Pyruvate is the anionic form of the three-carbon organic acid, pyruvic acid. FIG. 3 illustrates the role of pyruvate 304 as a key intermediate in the glycolytic 302 and pyruvate dehydrogenase 336 pathways, which are the main cellular pathways of biological energy production from carbohydrates. Pyruvate 304 serves as a biological fuel by being converted to acetyl-coenzyme A 305, which enters the tricarboxylic acid or Krebs cycle 306 where it is metabolized to produce ATP aerobically. Energy can also be obtained anaerobically from pyruvate via its conversion to lactate.

The addition of pyruvate into the composition enhances energy wasting cycles, promotes increased cellular respiration and increases endurance. Among possible mechanisms for this effect are increased generation of ATP and an increase in ATP phosphorylation potential. Another mechanism of the enhancing effect of pyruvate is the activation of pyruvate dehydrogenase, promoting pyruvate oxidation by inhibiting pyruvate dehydrogenase kinase. Pyruvate dehydrogenase is inactivated in ischemia myocardium. Yet another mechanism of pyruvate enhancement of cellular energy production is the reduction of cytosolic inorganic phosphate concentration. There are other possible mechanisms, such as enhanced sarcoplasmic reticular ion uptake, and release and reactive oxygen species scavenging. The pyruvate used in the invention may be a calcium salt.

The components of the composition provide synergistic effects whereby each is an integral ingredient in enhancing the cellular energy pathway. In particular, the components are supplemented together to avoid the homeostatic biofeedback mechanisms of the body. Where the above components are used separately, the biofeedback mechanisms of the body recognize an imbalance of critical factors and compensate by decreasing the natural production of the components. However, where the components are properly supplemented in the balanced amounts, the body is able to utilize the components for enhancing performance and endurance during physical activity.

In one embodiment of the invention the compounds listed are present in the following amounts:
creatine about 0.1-5 grams;
L-arginine-α-ketoglutarate about 0.1-5 grams;
D-ribose about 0.1-5 grams;
L-carnitine about 0.1-1 grams;
L-citrulline about 0.1-500 milligrams; and
Pyruvate about 0.1-3 grams.

In a preferred embodiment of the invention, the composition is formulated to provide particular amounts of the compounds listed above as a serving size. A serving size of the invention may include creatine in the amount of about 2-4 grams, L-arginine-α-ketoglutarate in the amount of about 1-3 grams, D-ribose in the amount of about 0.5-2.5 grams, L-carnitine in the amount of about 300-500 milligrams, L-citrulline in the amount of about 100-300 milligrams and pyruvate in the amount of about 400-600 milligrams.

In a more preferred embodiment of the invention, a serving size of the invention includes creatine in the amount of about 2.5-3.5 grams, L-arginine-α-ketoglutarate in the amount of about 1.5-2.5 grams, D-ribose in the amount of about 1-2 grams, L-carnitine in the amount of about 350-450 milligrams, L-citrulline in the amount of about 150-250 milligrams and pyruvate in the amount of about 450-550 milligrams. A composition formulated in these ranges may properly balance the above compounds and avoid the homeostatic biofeedback mechanisms of the body.

In another embodiment of the invention, the composition is formulated to avoid the homeostatic biofeedback mechanisms of the body through the proportional relationships of the compounds. Unless the composition contains the compounds listed above in the proper proportions, the body may decrease natural production or increase the breakdown of the compounds, therefore reducing the effectiveness of the composition. Therefore the composition is formulated where the amount of creatine in the composition is greater than the amount of L-arginine-α-ketoglutarate; the amount of L-arginine-α-ketoglutarate in the composition is greater than the amount of D-ribose; the amount of D-ribose in the composition is greater than the amount of pyruvate; the amount of pyruvate in the composition is greater than the amount of L-carnitine; and the amount of L-carnitine in the composition is greater than the amount of L-citrulline.

In another preferred embodiment of the invention, the composition is formulated to contain the following ratios of compounds in relation to each other:
Creatine: L-arginine-α-ketoglutarate in the ratio of 2-1.1:1
L-arginine-α-ketoglutarate: D-ribose in the ratio of 2-1.1:1
D-ribose: Pyruvate in the ratio of 4.5-1.5:1
Pyruvate:L-carnitine in the ratio of 1.1-1.5:1; and
L-carnitine:L-citrulline in the ratio of 1.25-4:1.

In a more preferred embodiment of the invention, the composition is formulated to contain the following ratios of compounds in relation to each other:
Creatine: L-arginine-α-ketoglutarate in the ratio of 1.5:1
L-arginine-α-ketoglutarate: D-ribose in the ratio of 1.33:1
D-ribose: Pyruvate in the ratio of 3:1
Pyruvate:L-carnitine in the ratio of 1.25:1; and
L-carnitine:L-citrulline in the ratio of 2:1.

In another embodiment of the invention, the composition may contain additional compounds including one or more of the following: α-lipoic acid, L-aspartate, succinate, glucomannan, and coenzyme Q10.

α-Lipoic acid is a disulfide compound that is a cofactor in vital energy-producing reactions in the body. Most of the metabolic reactions in which α-lipoic acid participates occur in the mitochondria. These functions include the oxidation of pyruvic acid (as pyruvate) by the pyruvate dehydrogenase enzyme complex and the oxidation of α-ketoglutarate by the α-ketoglutarate dehydrogenase enzyme complex. α-Lipoic acid is also a cofactor for the oxidation of branched-chain amino acids (L-leucine, L-isoleucine and L-valine) via the branched-chain α-keto acid dehydrogenase enzyme complex.

L-Aspartate is a protein amino acid naturally found in all life forms. L-Aspartate is considered a non-essential amino acid, where, under normal physiological conditions, sufficient amounts of the amino acid are synthesized in the body to meet the body's requirements. However, supplementation may be required where the body engages in prolonged physical activity. L-Aspartate is formed by the transamination of the Krebs cycle intermediate oxaloacetate. The amino acid serves as a precursor for synthesis of proteins, oligopeptides, purines, pyrimidines, nucleic acids and L-arginine. L-Aspartate is a glycogenic amino acid, and can also promote energy production via its metabolism in the Krebs cycle. In a preferred embodiment of the invention, L-aspartate is in the form of a potassium salt.

Coenzyme Q10 belongs to a family of substances called ubiquinones. Ubiquinones are lipophilic, water-insoluble substances involved in electron transport and energy production in mitochondria. Coenzyme Q10 in particular is an essential cofactor in the mitochondrial electron transport chain, where it accepts electrons from complex I and II, an activity that is vital for the production of ATP.

Glucomannan is a hydrocolloidal polysaccharide comprised of D-glucose and D-mannose residues bonded together in beta-1,4 linkages. The polysaccharide is also a soluble dietary fiber derived from konjac flour. Glucomannan acts as a polysaccharide energy source and may reduce hunger and appetite resulting in weight loss.

Succinate helps improve stamina and reduce damage to muscle tissue during intense exercise. Succinate is also produced as an intermediate in the Krebs Cycle as succinic acid. The composition of the invention may include succinate in the form of a potassium salt.

In an embodiment of the invention the compounds may be present in the following amounts:
α-lipoic acid about 0-100 milligrams;
L-aspartate about 0-1,000 milligrams;
succinate about 0-1,000 milligrams;
glucomannan about 0-1,000 milligrams; and
coenzyme Q10 about 0-100 milligrams.

In another embodiment of the invention, the following compounds may also be added to the composition containing creatine, L-arginine-α-ketoglutarate, D-ribose, L-carnitine, L-citrulline and pyruvate: betaine, glycine, vitamin A, vitamin C, vitamin B-12 (cyanocobalamin), folic acid, pantothenic acid (B-5), calcium, magnesium, zinc, sodium, vanadium (vanadyl sulfate), boron, *Camellia sinesis* and caffeine.

Betaine is a quarternary ammonium compound that is widely distributed in plants and animals. Betaine functions closely with other nutrients namely, S-adenosylmethionine (SAMe), folic acid, and vitamins B-6 and B-12, to eliminate homocysteine by transmethylation and reduce toxic levels of this substance in the bloodstream. High levels of homcysteine are associated with ischemic heart disease, strokes, peripheral vascular disease, osteoporosis and Alzheimer's disease.

Glycine is an amino acid is used in the biosynthesis of nucleic acids, bile acids, creatine, glutathione, porphyrin and other amino acids. Glycine is also a neurotransmitter in the central nervous system (CNS). Glycine and gamma-aminobutyric acid (GABA) are the major inhibitory neurotransmitters in the CNS.

Vitamin A is necessary for a broad range of bodily functions including normal functioning of the immune system, production of blood components (red blood cell production), production of vision pigments and maintenance of health in many body cells. B-carotene is a precursor of vitamin A.

Vitamin C (ascorbic acid) promotes healthy cell development in a number of organs and tissues. Vitamin C is an essential vitamin required for the proper formation and structural integrity of the musculoskeletal system, particularly in collagen, tendons and ligaments and bone. Additionally, vitamin C has been shown to play an important role in wound healing, resistance to infection and the reduction oxidative stress.

Vitamin B-12 (cyanocobalamin) stimulates appetite, metabolism, mental function and growth. Additionally, B-12 is vital for blood (red blood cell) formation and a healthy nervous system. Apart from behaving as a stimulator of a number of body processes, B-12 performs coenzyme action in tandem with other compounds, such as folic acid in utilizing amino acids and carrying out one carbon transfer.

Folic acid plays a significant role in red blood cell formation, RNA and DNA synthesis, amino acid metabolism, cell division and purine/pyrimidine synthesis. Due to the role of folic acid in cell formation its presence is required for a healthy brain, immune system, digestive system and nervous system. Furthermore folic acid also is essential for one carbon metabolism.

Pantothenic acid (B-5) is used by the body in the metabolism and efficient utilization of fats and breakdown of carbohydrates. Additionally, pantothenic acid assists in the formation of hormones, and components necessary for immune function.

Calcium is a major mineral component of bone health along with phosphorus, magnesium, sodium, and potassium and is essential for developing and maintaining healthy bones and teeth. Apart from its role as a mineral in bone development, calcium is used by every cell in the body and is critical for blood clotting, muscle contraction, and nerve transmission.

Magnesium, like calcium, is an important mineral that performs in nerve function, muscle function, and bone cell production. Inadequate blood magnesium levels are known to result in low blood calcium levels. Magnesium is also involved in energy generating bodily processes where the mineral is used to break down sugar stored in the liver to produce energy.

Zinc is an essential element in human and animal nutrition with a wide range of biological roles. Physiologically, zinc is vital for growth and development, sexual maturation and reproduction, dark vision adaptation, olfactory and gustatory activity, insulin storage and release and for a variety of host immune defenses, among other things.

Chromium is an essential trace mineral that assists in the regulation of normal sugar (glucose) utilization in cells by maintaining the function of insulin, the hormone that regulates body sugar. Chromium may also have a role in improving fat (lipid) and lean mass profiles.

Sodium is the primary cation in extracellular fluids. As the primary cation in the body, sodium is indispensable for nerve impulse transmission, muscle contraction and pH balance.

Potassium is an essential macromineral in human nutrition with a wide range of biochemical and physiological roles. Among other things, it is important in the transmission of nerve impulses, the contraction of cardiac, skeletal and smooth muscle, the production of energy, the synthesis of nucleic acids, the maintenance of intracellular tonicity and the maintenance of normal blood pressure.

Vanadium (vanadyl sulfate) is a metallic element that plays a number of roles in the human body. Notably, vanadium affects a number of important enzymes in cellular energy production such as NaK-ATPase, phosphoryl transferase, adenylate cyclase, and protein kinases. Additionally, vanadium compounds may mimic insulin or other cells leading to regulation of metabolism of glucose, lipids, the effect of growth factors on cells, creatine uptake and insulin function.

Boron is another trace mineral in the human body that may be required for the proper activity of vitamin D and may further contribute to bone integrity. While the exact mechanism of action of boron has not been clarified at this time it is believed that boron and calcium actions are inter-related or that the two elements affect similar systems, including the modification of hormone action, the alteration of cell membrane characteristics and/or trans-membrane signaling. Boron may play a role in calcium metabolism and as such may aid in the prevention of osteoporosis.

*Camellia sinesis* contains antioxidant polyphenols which support lipid oxidation and provide a source of energy.

Caffeine improves central processes involved in arousal and motivation by acting as an A1 and A2 adenosine receptor antagonist. The action of caffeine of increases dopamine and nordrenaline release, enhances physical performance, improves cognitive performance, improves vigilance and facilitates speed of target acquisition.

In another embodiment of the invention, the composition may further include a number of non-active compounds, such as effervescent combinations, diluents, buffers, preservatives, desiccants, thickeners, fillers, flavorings, sweeteners, colorings and any other excipients or non-active ingredients known in the art. The composition maybe in the form of a powder, liquid, capsule, tablet or chewing gum and/or may be formed as part of a food product. In a preferred embodiment, the composition is a powder that may be solubilized in a liquid for ingestion.

In a preferred embodiment of the invention, the composition includes an effervescent combination. The effervescent combination may include any combination of at least one acid and at least one base known in the art to produce an effervescent effect that is safe for use in food or pharmaceuticals. Examples of suitable acids may include citric acid, tartaric acid, aspartic acid or malic acid and combinations thereof. Examples of suitable bases may include sodium carbonate, potassium bicarbonate or sodium bicarbonate and combinations thereof.

In another embodiment of the invention, the composition is administered to a subject to enhance performance during physical activity. The enhanced performance may be measured as increase relative intensity of physical activity, increased endurance during physical activity and increased muscle mass as the result of physical activity. In a preferred embodiment, the composition is administered 15 to 30 minutes before the subject begins the physical activity to allow the composition to be absorbed by the body. In another preferred embodiment, the composition powder containing an effervescent is solubilized in a liquid whereby producing an effervescent effect. In particular, the solubilizing liquid may include water or other aqueous liquids. The composition powder is added to 8 fluid ounces of water and shaken or stirred to allow the mixture to effervesce for 2-5 minutes before ingestion.

Example: The following table is an example of one embodiment of the invention.

| Ingredient | Amount per serving |
| --- | --- |
| Vitamin A (as beta-carotene) | 1,250 IU |
| Vitamin C (as ascorbic acid) | 180 mg |
| Folic Acid | 100 mg |
| Vitamin B-12 (as cyanocobalamin) | 30 mcg |
| Pantothenic acid (as calcium pantothenate) | 20 mg |
| Calcium (as calcium citrate) | 200 mg |
| Magnesium (as magnesium citrate) | 40 mg |
| Zinc (as zinc gluconate) | 3 mg |
| Chromium (as chromium citrate) | 60 mcg |
| Sodium (as bicarbonate) | 140 mg |
| Potassium (as bicarbonate) | 150 mg |
| Vanadium (as amino acid chelate) | 4 mg |
| Boron (as amino acid chelate) | 100 mcg |
| Creatine (monohydrate and citrate) | 3 g |
| Betaine (as HCl) | 100 mg |
| L-Carnitine | 400 mg |
| D-Ribose | 1.5 g |
| Calcium pyruvate | 500 mg |
| L-Arginine-alpha-ketoglutarate | 2 g |
| Glycine | 500 mg |
| L-Citrulline | 200 mg |
| *Camellia sinensis* | 500 mg |
| Caffeine | 70 mg |

The formulation of the example was tested on a cohort of elite athletes. The athletes were members of a major professional sports team. Professional trainers and nutritionists employed by the team have formulated a workout training regimen that is consistent from year to year with regard to the athletes who are members of the team. The team uses a measurement of the efficacy the workout regimen based on a relative strength index in which a score of 100% indicates the athlete is performing at maximum efficiency according to their relative strength. This measurement is called the relative intensity measurement. A relative intensity of 100% is the desired goal for each athlete. The scale for measuring relative intensity is illustrated in FIG. 4.

The formulation was given to the athletes over the course of a nine week workout regimen. The athletes' workout results were measured according to a relative intensity index. The use of relative intensity illustrates the individual improvement of each athlete and removes the variables of size, age and total strength of athlete. The athletes' scores using the formulation (2004) were compared to scores from the same time in the workout phase ($2^{nd}$ week) during the previous year (2003) when the athletes were not taking the formulation. The other comparison was based on the athletes taking the formulation compared with another group of athletes following the same workout regimen who did not take the formulation of the example. The comparison of results of the athletes taking the formulation against the athletes not taking the formulation was performed on the year end data. The results of the testing are shown in the following graphs, where the values are based on an average of relative intensities of the athletes tested for a number of power lifting exercises including the squat, power-clean and bench press.

As shown in the charts above, the athletes taking the formulation of the example showed greatly improved relative intensity during the workout regime when compared with data from the previous year that measured physical exercise performed without taking the formulation. Even more significantly, the athletes taking the formulation showed much higher average relative intensity after completion of the workout regimen than the athletes who were not taking the formulation of the example. The data presented above shows the exceptional effects of taking the formulation of the invention and its unexpected effects over other types of nutritional supplements.

Although the present invention has been described in detail with particular reference to preferred embodiments thereof, it should be understood that the invention is capable of other different embodiments, and its details are capable of modifications in various obvious respects. As is readily apparent to those skilled in the art, variations and modifications can be affected while remaining within the spirit and scope of the invention. Accordingly, the foregoing disclosure, description, and figures are for illustrative purposes only, and do not in any way limit the invention, which is defined only by the claims.

What is claimed is:

1. A composition for enhancing cellular energy comprising:
   creatine: L-arginine-α-ketoglutarate in the ratio of 1.5:1
   L-arginine-α-ketoglutarate: D-ribose in the ratio of 1.33:1
   D-ribose: pyruvate in the ratio of 3:1
   pyruvate: L-carnitine in the ratio of 1.25:1;
   L-carnitine: L-citrulline in the ratio of 2:1; and
   one or more ingredients selected from the group consisting of betaine, caffeine, α-lipoic acid, L-aspartate, glucomannan, succinate, glycine, *Camellia sinesis*, calcium, magnesium, zinc, sodium, vanadium, and boron;
   the composition increasing the relative intensity of physical activity in mammals, increasing the endurance of animals performing a physical activity, and increasing the muscle mass of mammals.

2. The composition of claim 1, further comprising betaine, caffeine, α-lipoic acid, L-asp artate, glucomannan, succinate, glycine, *Camellia sinesis*, calcium, magnesium, zinc, sodium, vanadium, and boron.

3. The composition of claim 1, wherein the amount of creatine is 2.5-3.5 grams.

4. The composition of claim 1, wherein the amount of L-arginine-α-ketoglurarate is 1.5-2.5 grams.

5. The composition of claim 1, wherein the amount of D-ribose is 1-2 grams.

6. The composition of claim 1, wherein the amount of pyruvate is 450-550 milligrams.

7. The composition of claim 1, wherein the amount of L-carnitine is 350-450 milligrams.

8. The composition of claim 1, wherein the amount of L-citrulline is 150-250 milligrams.

9. A method of enhancing the cellular energy of a mammal by administering the composition of claim 1.

10. The method of claim 9, further comprising administering the composition to a mammal performing a physical activity 15-30 minutes before initiation of the physical activity.

* * * * *

UNITED STATES PATENT AND TRADEMARK OFFICE
CERTIFICATE OF CORRECTION

| | | |
|---|---|---|
| PATENT NO. | : 7,645,742 B2 | Page 1 of 1 |
| APPLICATION NO. | : 11/157991 | |
| DATED | : January 12, 2010 | |
| INVENTOR(S) | : Stohs | |

Figure 5:
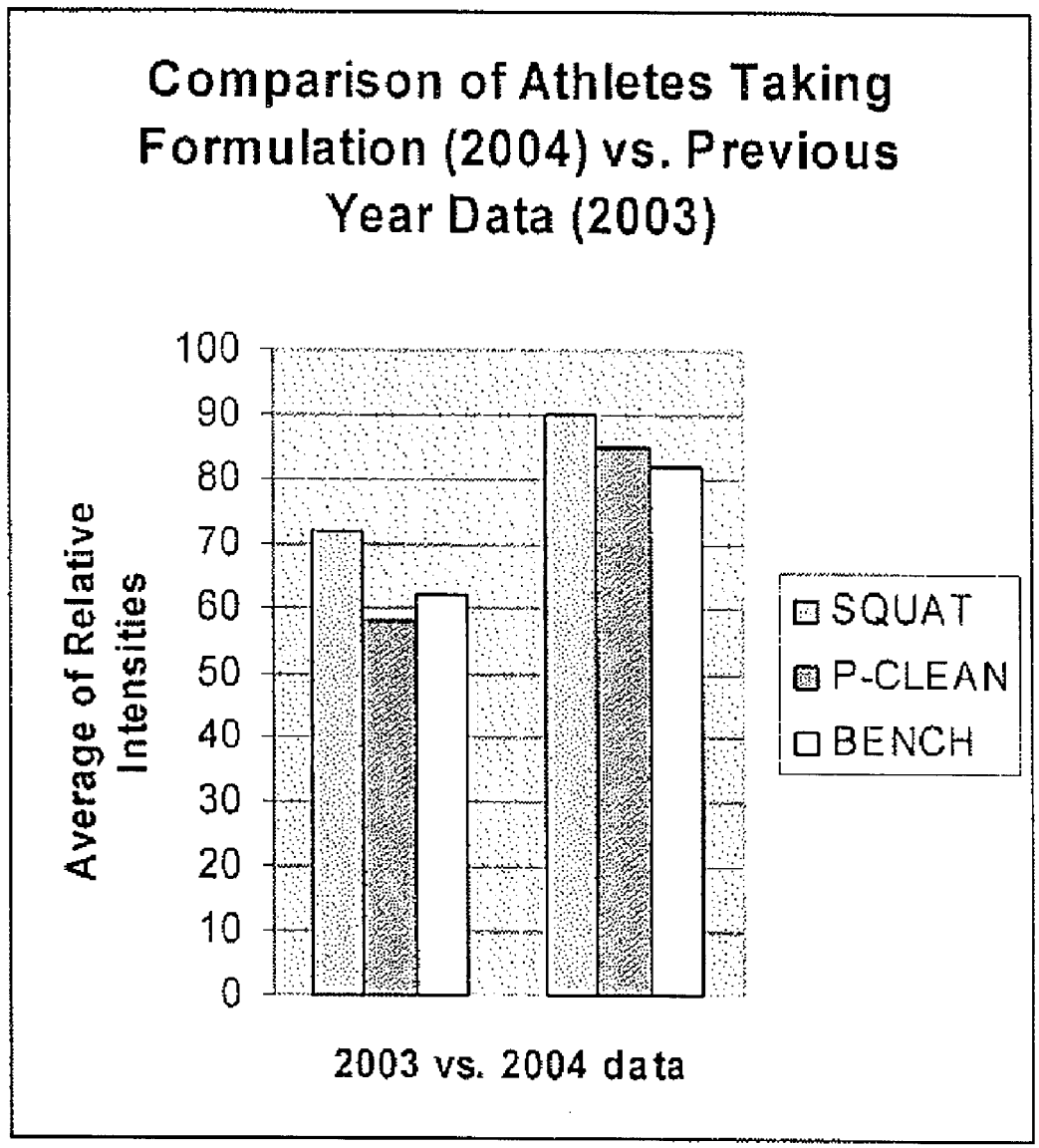
FIG. 5 illustrates the relative intensity of athletes taking the formulation, during a workout regimen when compared with data from the previous year that measured physical exercise performed without taking the formulation.
Figure 6:
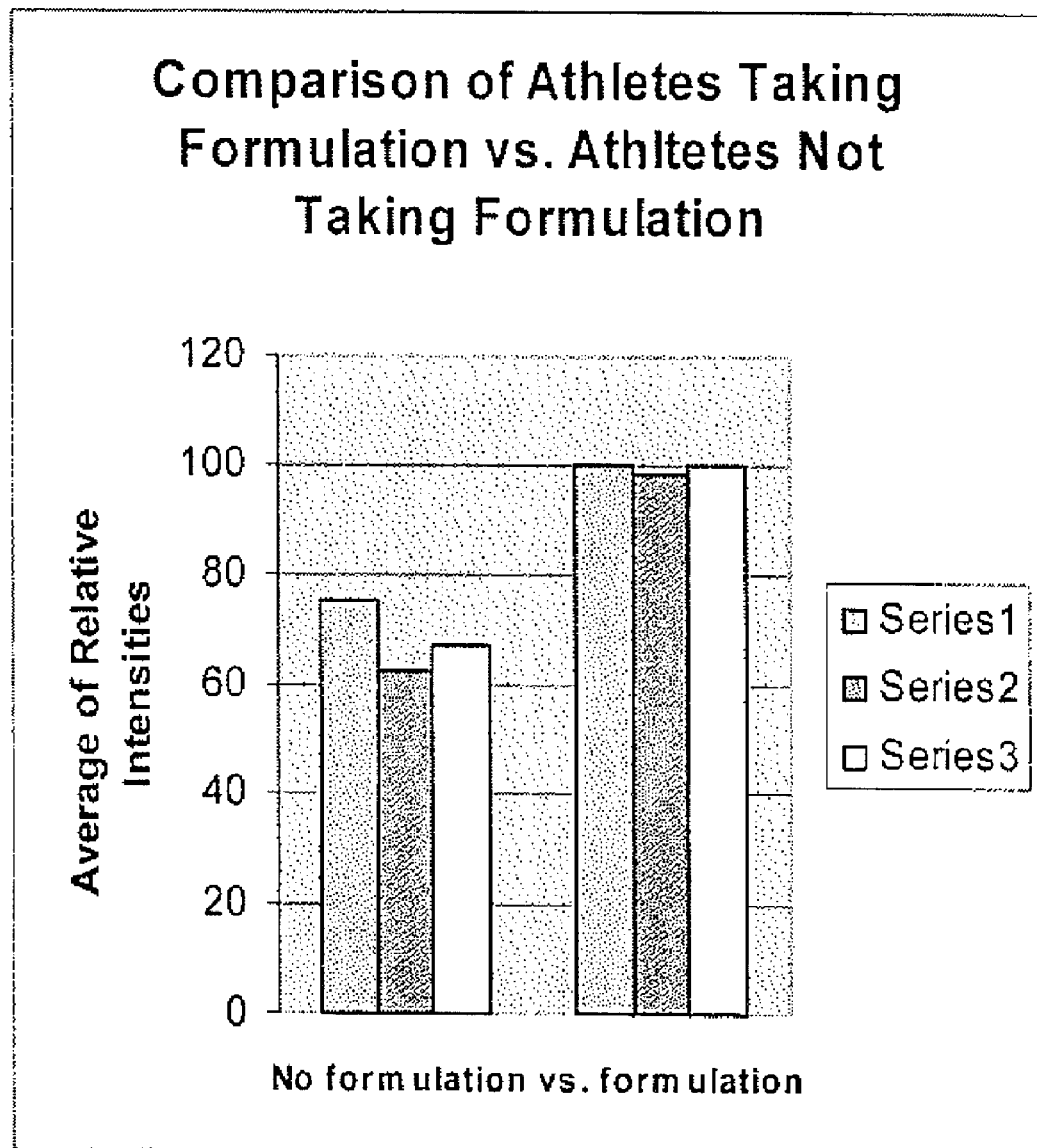
FIG. 6 illustrates a comparison of the relative intensity of the same workout regimen performed by athletes taking the formulation as compared to athletes who were not taking the formulation, wherein Series 1 represents Squat, Series 2 represents P-clean, and Series 3 represents Bench.

It is certified that error appears in the above-identified patent and that said Letters Patent is hereby corrected as shown below:

On column 11, line 61, replace "As shown in charts above" with --As shown in Figures 5 and 6--

On column 12, line 7, replace "The data presented above" with --The data presented in Figures 5 and 6--

Signed and Sealed this

Sixteenth Day of February, 2010

David J. Kappos
*Director of the United States Patent and Trademark Office*